US012661064B2

(12) United States Patent
Yanase

(10) Patent No.: US 12,661,064 B2
(45) Date of Patent: Jun. 23, 2026

(54) BODY MOTION SENSOR, PROGRAM, AND INFORMATION PRESENTATION SYSTEM

(71) Applicant: icuco Inc., Aichi (JP)

(72) Inventor: Yoichi Yanase, Aichi (JP)

(73) Assignee: icuco Inc., Aichi (JP)

( * ) Notice: Subject to any disclaimer, the term of this patent is extended or adjusted under 35 U.S.C. 154(b) by 776 days.

(21) Appl. No.: 17/910,985

(22) PCT Filed: Mar. 1, 2021

(86) PCT No.: PCT/JP2021/007643
§ 371 (c)(1),
(2) Date: Sep. 12, 2022

(87) PCT Pub. No.: WO2021/187066
PCT Pub. Date: Sep. 23, 2021

(65) Prior Publication Data
US 2023/0147448 A1 May 11, 2023

(30) Foreign Application Priority Data

Mar. 16, 2020 (JP) ................................. 2020-045056

(51) Int. Cl.
*A61B 5/00* (2006.01)
*A61B 5/11* (2006.01)
(52) U.S. Cl.
CPC .............. *A61B 5/6802* (2013.01); *A61B 5/11* (2013.01); *A61B 2562/02* (2013.01)
(58) Field of Classification Search
CPC ..... A61B 5/6802; A61B 5/11; A61B 2562/02; A44B 99/00; G01P 15/18
See application file for complete search history.

(56) References Cited

U.S. PATENT DOCUMENTS 10,022,053 B2 * 7/2018 Li ...................... A61B 5/14551
10,349,847 B2 * 7/2019 Kwon ................ A61B 5/14552
(Continued)

FOREIGN PATENT DOCUMENTS

CN 104224131 12/2014
CN 104434079 3/2015
(Continued)

OTHER PUBLICATIONS

International Search Report issued in International Bureau of WIPO Patent Application No. PCT/JP2021/007643, dated May 18, 2021, along with an English translation thereof.
(Continued)

*Primary Examiner* — May A Abouelela
(74) *Attorney, Agent, or Firm* — Greenblum & Bernstein, P.L.C.

(57) ABSTRACT

A body motion sensor according to the present disclosure includes one or a plurality of detecting units which is placed in a casing attachable so as to be in contact with a body, and which is capable of detecting a body situation, and a control unit capable of controlling a transmission of information to an external device based on a detection signal from the detecting unit. The detecting unit includes at least an optical sensor. The control unit determines a contact state of the casing with the body of a wearing person in accordance with the detection signal from the optical sensor, and decides an information content to be transmitted to the external device based on the detection signal from the detecting unit in accordance with a determination result.

4 Claims, 10 Drawing Sheets

(56)                References Cited

U.S. PATENT DOCUMENTS

| | | | |
|---|---|---|---|
| 10,357,165 B2 * | 7/2019 | Yoon | A61B 5/02141 |
| 10,497,197 B2 * | 12/2019 | Yamamoto Murakami | |
| | | | G10L 17/10 |
| 10,520,378 B1 * | 12/2019 | Brown | A61B 5/6801 |
| 10,568,527 B2 * | 2/2020 | Yoon | A61B 5/021 |
| 10,820,858 B2 * | 11/2020 | Yoon | A61B 5/0245 |
| 11,276,488 B2 * | 3/2022 | Nasedkin | A61B 5/389 |
| 2013/0310636 A1 | 11/2013 | Krans et al. | |
| 2014/0012146 A1 | 1/2014 | Fukuda | |
| 2014/0358012 A1 * | 12/2014 | Richards | H04W 4/027 |
| | | | 600/479 |
| 2014/0379292 A1 * | 12/2014 | Ara | A61B 5/11 |
| | | | 702/141 |
| 2015/0148623 A1 * | 5/2015 | Benaron | A61B 5/681 |
| | | | 600/306 |
| 2017/0035356 A1 | 2/2017 | Yamamoto et al. | |
| 2017/0112398 A1 | 4/2017 | Narusawa | |
| 2017/0224218 A1 * | 8/2017 | Tanaka | A61B 5/02438 |
| 2017/0311831 A1 * | 11/2017 | Freer | A61B 5/16 |
| 2017/0312427 A1 | 11/2017 | Steger et al. | |
| 2019/0046048 A1 * | 2/2019 | Kitagawa | A61B 5/02116 |
| 2019/0150854 A1 * | 5/2019 | Chung | G06F 1/325 |
| 2019/0209853 A1 * | 7/2019 | Kim | A61N 1/3987 |
| 2021/0113139 A1 * | 4/2021 | Hiratsuka | A61B 5/742 |

FOREIGN PATENT DOCUMENTS

| | | |
|---|---|---|
| CN | 106951723 | 7/2017 |
| CN | 107224277 | 10/2017 |
| JP | 2005-270546 A | 10/2005 |
| JP | 2014-12072 A | 1/2014 |
| JP | 2014-502188 A | 1/2014 |
| JP | 2015-188498 A | 11/2015 |
| JP | 2016-67811 A | 5/2016 |
| JP | 2016-152859 A | 8/2016 |
| JP | 2017-164537 A | 9/2017 |
| WO | 2005/092180 | 10/2005 |
| WO | 2012/069962 | 5/2012 |
| WO | 2015/146138 | 10/2015 |

OTHER PUBLICATIONS

Office Action issued by the China National Intellectual Property Administration (CNIPA) in Chinese Patent Application No. 202180019566.7, dated Feb. 18, 2025, together with an English language translation.

Written Opinion issued in International Bureau of WIPO Patent Application No. PCT/JP2021/007643, dated May 18, 2021, along with an English translation thereof.

Office Action issued by the China National Intellectual Property Administration (CNIPA) in Chinese Patent Application No. 202180019566.7, dated Sep. 20, 2025, together with an English language translation.

* cited by examiner

FIG. 8

| | BREATHING | BREATHING STATE | HEART RATE | ATTACHMENT STATUS | ACCELEROMETER | | PULSE SENSOR | | PHYSICAL CONDITION ALERT | DETACHMENT NOTIFICATION |
|---|---|---|---|---|---|---|---|---|---|---|
| | | | | | MIN-MAX | FFT | LIGHT INTENSITY | FFT | | |
| A | PRESENT | NORMAL | NORMAL | ATTACHED | NORMAL | NORMAL | NORMAL | NORMAL | OFF | OFF |
| B | PRESENT | NORMAL | NORMAL | DETACHED | ABNORMAL | NORMAL | ABNORMAL | ABNORMAL | OFF | OFF (ON) |
| | | | | | ABNORMAL | ABNORMAL | ABNORMAL | ABNORMAL | OFF | OFF (ON) |
| | | | | | NORMAL | NORMAL | ABNORMAL | ABNORMAL | OFF | OFF (ON) |
| C | PRESENT (AGONAL BREATHING) | ABNORMAL | ABNORMAL | ATTACHED | NORMAL | ABNORMAL | ABNORMAL | ABNORMAL | ON | OFF |
| D | ABSENT | ABNORMAL | NORMAL | ATTACHED | ABNORMAL | ABNORMAL | NORMAL | NORMAL | ON | OFF |
| E | ABSENT | ABNORMAL | ABNORMAL | ATTACHED | ABNORMAL | ABNORMAL | NORMAL | ABNORMAL | ON | OFF |
| F | ABSENT | ABNORMAL | NORMAL | DETACHED | ABNORMAL | NORMAL | ABNORMAL | ABNORMAL | OFF (ON) | ON |
| | | | | | ABNORMAL | ABNORMAL | ABNORMAL | ABNORMAL | OFF (ON) | ON |
| G | PRESENT | NORMAL | ABNORMAL | DETACHED | ABNORMAL | NORMAL | ABNORMAL | ABNORMAL | OFF (ON) | ON |
| | | | | | NORMAL | ABNORMAL | ABNORMAL | ABNORMAL | OFF (ON) | ON |
| H | PRESENT (AGONAL BREATHING) | ABNORMAL | ABNORMAL | DETACHED | NORMAL | NORMAL | ABNORMAL | ABNORMAL | OFF (ON) | ON |
| | | | | | ABNORMAL | ABNORMAL | ABNORMAL | ABNORMAL | OFF (ON) | ON |
| I | ABSENT | ABNORMAL | ABNORMAL | DETACHED | ABNORMAL | ABNORMAL | ABNORMAL | ABNORMAL | OFF (ON) | ON |

BODY MOTION SENSOR, PROGRAM, AND INFORMATION PRESENTATION SYSTEM

TECHNICAL FIELD

The present disclosure relates to a body motion sensor and a program for executing processes relating to the body motion sensor.

BACKGROUND ART

Regarding a sensor attached to a body, technologies disclosed in the following Patent Documents are example background arts.

Patent Document 1 discloses a biological information detecting system which accumulates pulse wave information and body motion information, and which appropriately determines the sleeping condition of a user by utilizing the change information of the pulse wave information and the change information of the body motion information.

Moreover, Patent Document 2 discloses a biological information processing system that controls an operation target device based on mental state information estimated from the biological information of a user who operates the operation target device, and on working condition information on the operation target device operated by the user.

CITATION LIST

Patent Literatures

Patent Document 1: JP2016-067811A
Patent Document 2: JP2016-152859A

SUMMARY OF INVENTION

Technical Problem

A childminder, a babysitter, or parents have large burdens for taking care of an infant.

For example, it is difficult for such a person to look aside even if an infant is taking a nap. Hence, the work burdens for a childminder, etc., or the childcare burdens for parents are quite large.

In recent years, as a scheme for reducing such burdens, it is attempted to attach a body motion sensor to an infant so as to enable detection of abnormalities in the infant, such as the abnormality in pulse, the abnormality in body temperature and a state in which there is no body motion. In this case, the body motion sensor outputs an alert when detecting the abnormality in the infant, so that a childminder, etc., can be aware of such abnormality. This spares the need for the childminder, etc., to always stay around the infant.

However, an alert may be output when the body motion sensor is not attached properly, or when the attachment state of the body motion sensor becomes not suitable for detection because of the motion, etc., of the infant.

In this case, although the infant is in a normal condition, it is necessary for the childminder, etc., to immediately run up to the infant and to check the condition thereof. In particular, displacement of the attached body motion sensor often occurs due to the roll-over of the infant while taking a nap, and to the activity during playing. This increases the output frequency of the alert, unintendedly increasing the work burdens in some cases.

Accordingly, in view of such technical problems, an objective of the present disclosure is to enable an appropriate output of an alert in accordance with the attachment state of a body motion sensor.

Solution to Problem

A body motion sensor according to the present disclosure includes:

one or a plurality of detecting units which is placed in a casing attachable so as to be in contact with a body of a wearing person, and which is capable of detecting a body situation of the wearing person; and a control unit capable of controlling a transmission of information to an external device based on a detection signal from the detecting unit, in which the detecting unit includes at least an optical sensor, and in which the control unit determines a contact state of the casing with the body of the wearing person in accordance with the detection signal from the optical sensor, and decides an information content to be transmitted to the external device based on the detection signal from the detecting unit in accordance with a determination result.

Accordingly, the information content to be transmitted to the external device is decided with not only the body situation of the wearing person but also the contact state of the casing including the detecting unit with the body of the wearing person being taken into consideration.

In the above-described body motion sensor, the control unit:

determines the contact state of the casing with the body of the wearing person when detecting an abnormality in the wearing person based on the body situation of the wearing person detected by the detecting unit;

when determining that the casing is in contact with the body of the wearing person, transmits, to the external device, alert information indicating the abnormality in the wearing person; and when determining that the casing is not in contact with the body of the wearing person, transmits, to the external device, a notification signal indicating a non-contact state.

Accordingly, even if the abnormality in the wearing person is detected, depending on the contact state of the casing, the alert information may be not transmitted to the external device.

A program according to the present disclosure causes an arithmetic processing device to execute:

a process of obtaining a detection signal from one or a plurality of detecting units which is placed in a casing attachable so as to be in contact with a body of a wearing person, and which is capable of detecting a body situation of the wearing person; and a process of determining a contact state of the casing with the body of the wearing person in accordance with the detection signal from an optical sensor that is one of the detecting units, and deciding an information content to be output based on the detection signal from the detecting unit in accordance with a determination result.

That is, the arithmetic processing device is the controller in the body motion sensor, the controller in a terminal device that operates in conjunction with the body motion sensor, etc.

An information presentation system according to the present disclosure includes:

the above-described body motion sensor; and a terminal device presenting information based on the information transmitted from the body motion sensor.

The information presentation system is achieved by mutual communication between the body motion sensor and the terminal device.

Advantageous Effects of Invention

According to the present disclosure, a false output of an alert originating from a false detection is addressed, and thus the work burdens for a childminder, etc., and the childcare burdens for a parental guardian can be reduced by an appropriate output of an alert.

BRIEF DESCRIPTION OF DRAWINGS

FIG. 8 is a diagram for describing information obtained by the body motion sensor according to the embodiment;

DESCRIPTION OF EMBODIMENTS

An embodiment will be described with reference to FIG. 1 to FIG. 10.

Note that a structure illustrated in the figure to be referred in order to describe the embodiment indicates major necessary components and the peripheral structure thereof extracted to carry out the embodiment. Moreover, the figures are merely examples, and the thickness, the relation with a planar dimension, the ratio, etc., of each component illustrated in the figure are merely examples. Hence, various changes can be made in accordance with a system design, etc., without departing from the scope and spirit of the present disclosure.

1. OUTLINE OF INFORMATION PRESENTATION SYSTEM

The outline of an information presentation system 100 according to an embodiment will be described with reference to FIG. 1.

Figure 1:
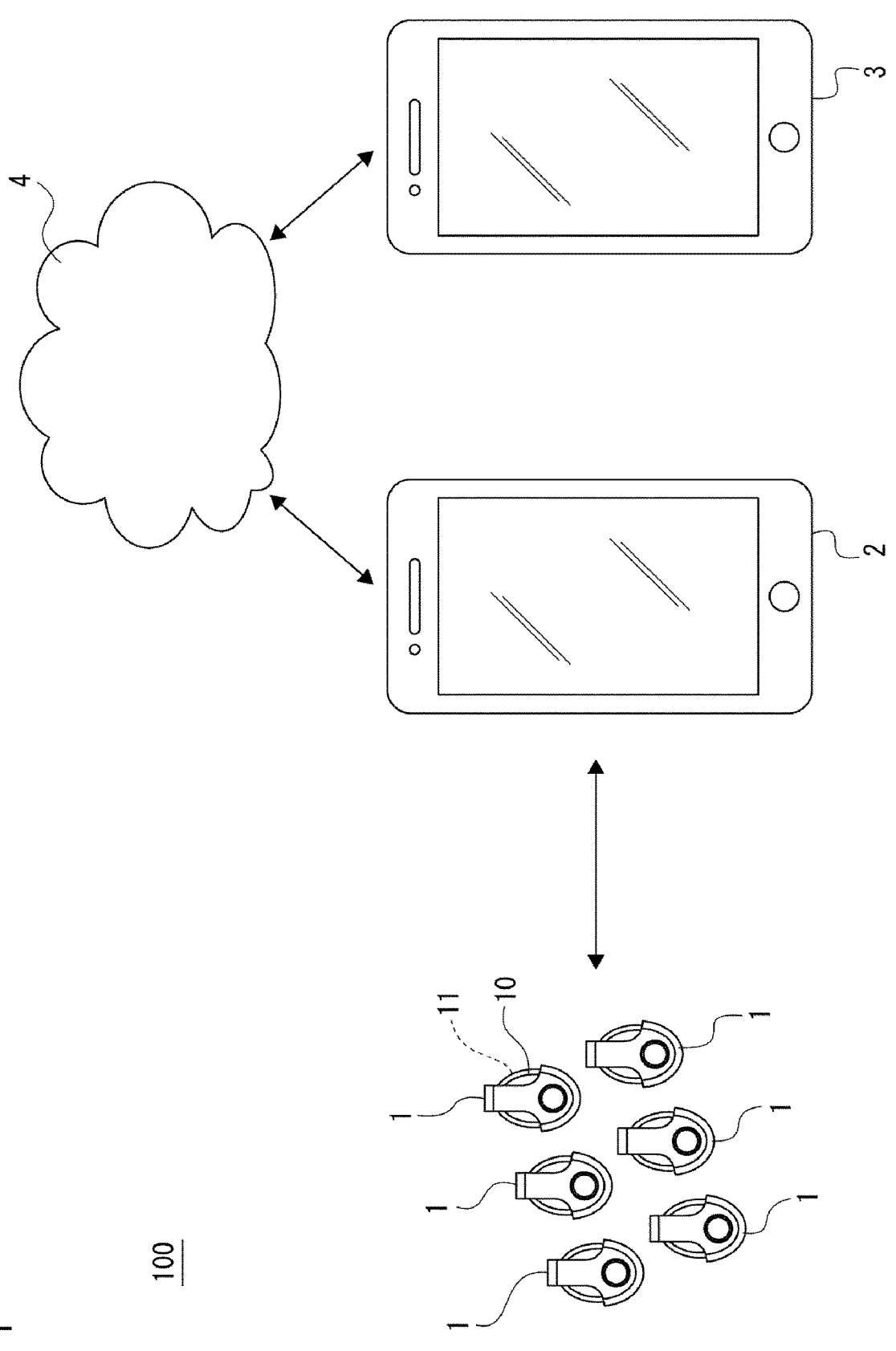
FIG. 1 is a diagram for describing a configuration of an information presentation system according to an embodiment of the present disclosure.

FIG. 1 illustrates a configuration of the information presentation system 100 that accomplishes a service utilizing a body motion sensor 1.

The information presentation system 100 includes body motion sensors 1, portable terminals 2 and 3 like smartphones, and a cloud server 4. Each body motion sensor 1 is communicable with the portable terminal 2 by near field communication like Bluetooth (registered trademark). Moreover, the portable terminals 2 and 3 are communicable with the cloud server 4 by communication, such as Wireless Fidelity (Wi-Fi: registered trademark) or Long Term Evolution (LTE: registered trademark).

Each body motion sensor 1 is attached to the clothing, etc., of an infant Hm.

The body motion sensor 1 includes one or a plurality of detecting units 11 in a casing 10. More specifically, as the detecting units 11, sensors, such as an optical pulse sensor 111, a triaxial accelerometer 112 and a temperature sensor 113 to be described later, are loaded, and the back surface of the casing 10 serves as a sensing surface.

Figure 2:
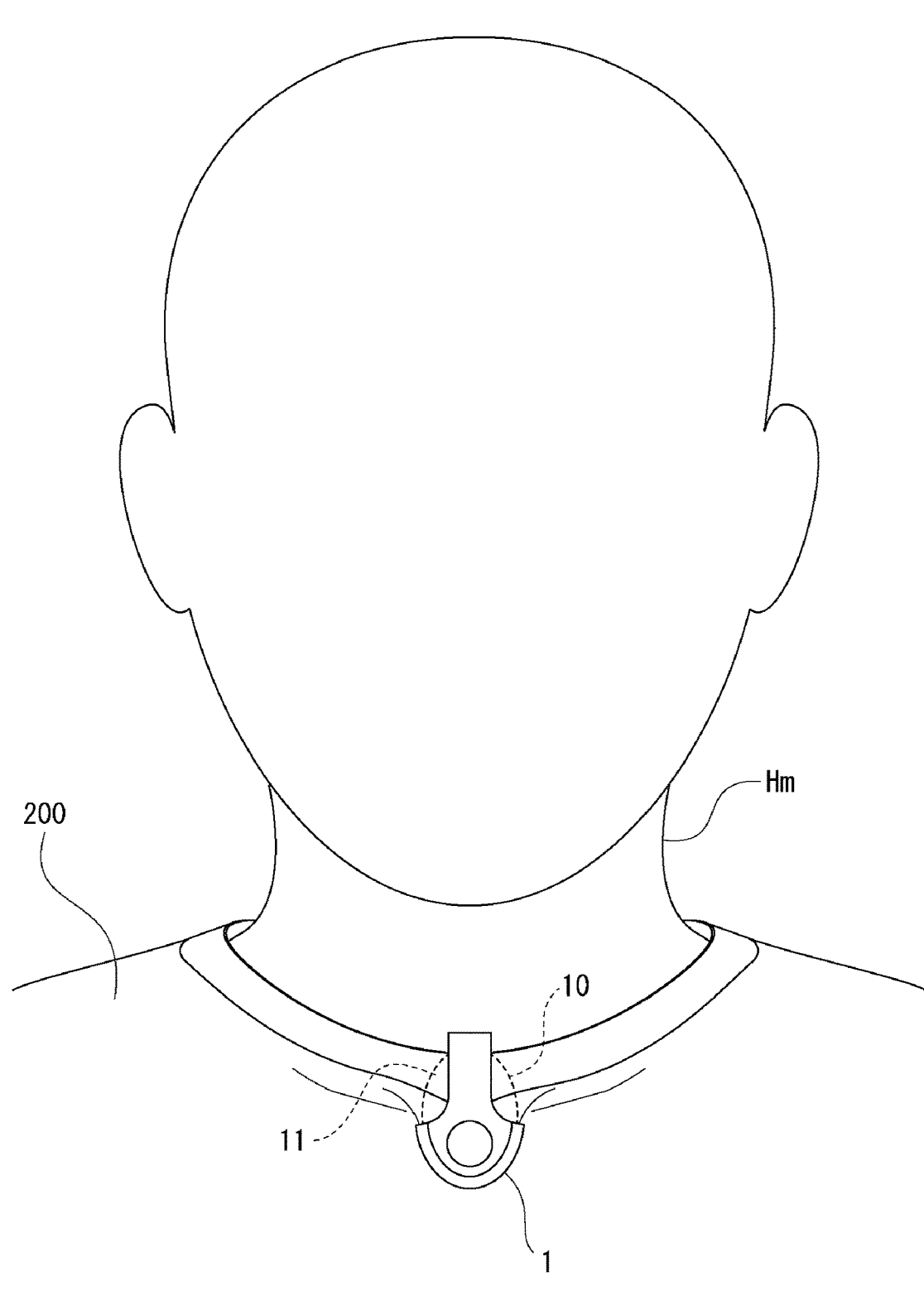
FIG. 2 is a diagram for describing an attached state of the fastener according to an embodiment.

By attaching the body motion sensor 1 so as to pinch a fabric 200 of the clothing of the infant Hm as illustrated in FIG. 2, the back surface of the casing 10 contacts the skin of the infant Hm, and can sense a pulse, a body motion, and a body temperature.

Returning to FIG. 1, the body motion sensor 1 communicates with the portable terminal 2 like a smartphone of a childminder, a babysitter, etc., (the following description will be given of an example case in which such a person is a childminder). In particular, the body motion sensor 1 detects the abnormality in the physical condition of the infant Hm based on detection of sensing information which indicates the body situations of the infant Hm, such as a pulse, a body motion, and a body temperature, and can transmit alert information to the portable terminal 2. The abnormality in the infant Hm in this example are abnormalities of breathing, heart rate, body motions, sleeping postures, a body temperature, etc.

An application program corresponding to the body motion sensor 1 is installed in the portable terminal 2, and an alert is output by image, sound, vibration, etc., in accordance with the alert information from the body motion sensor 1.

Hence, even if a childminder does not always stay around the sleeping infant Hm, the childminder can grasp an occurrence of an abnormal condition of the infant Hm by the alert.

Note that the body motion sensor 1 may transmit the sensing information, such as a pulse, a body motion, and a body temperature, to the portable terminal 2. In that case, in the portable terminal 2, the abnormality in the infant Hm is detected from each piece of the sensing information, so that an alert can be output by image, sound, vibration, etc.

Figure 3:
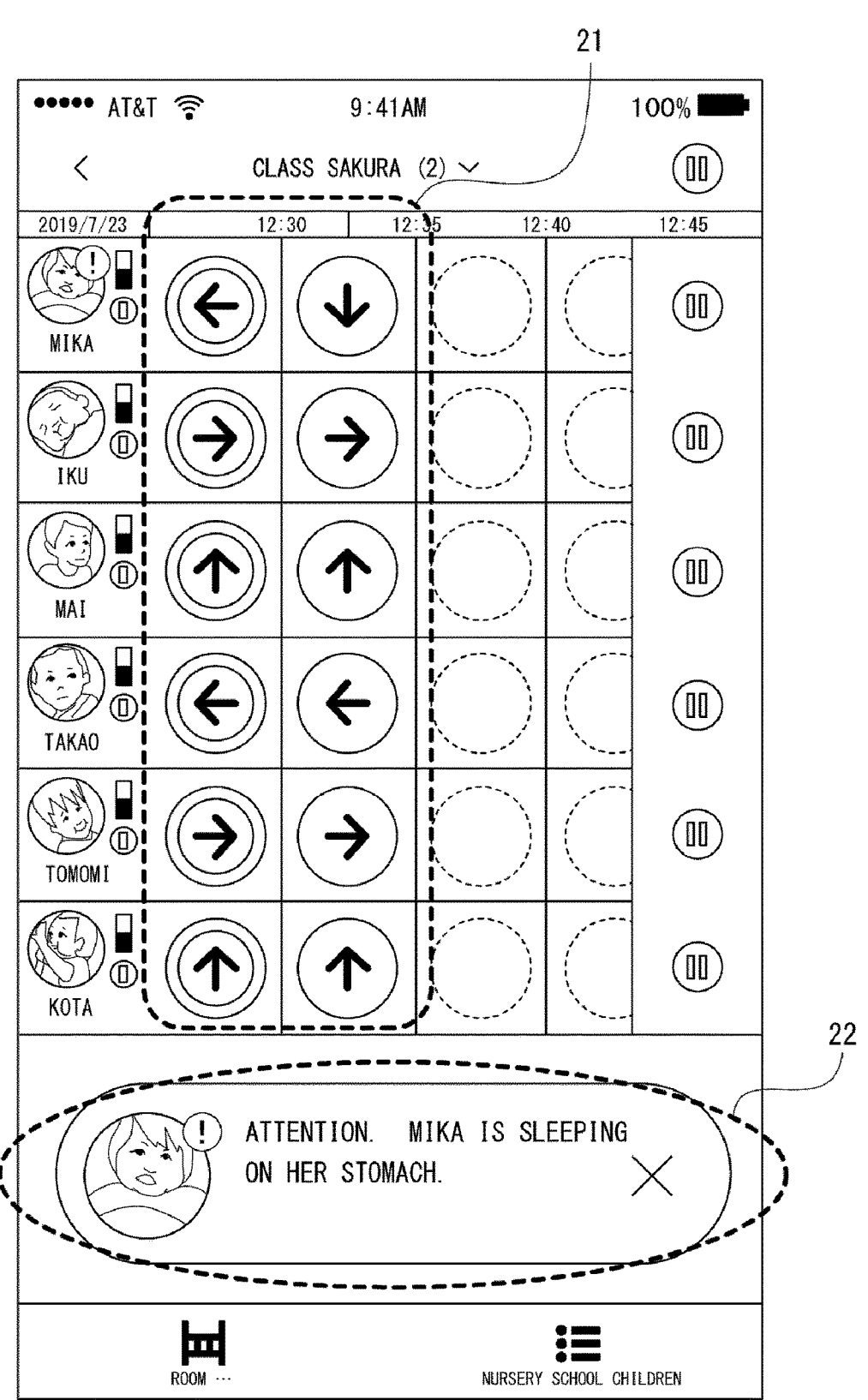
FIG. 3 is a diagram for describing an example screen of a terminal device according to an embodiment.

FIG. 3 illustrates an example screen to be displayed on the portable terminal 2 utilized by the childminder.

Displayed on a screen region 21 of the portable terminal 2 are the state of each infant Hm whom the childminder has a responsibility for childcare from a parental guardian, and the battery remaining level of each body motion sensor 1 attached to each infant Hm, etc. For example, a record of the sleeping posture (the direction of the body) of each infant Hm for each time slot is displayed on the portable terminal 2. Note that although it is not illustrated in the figure, various information, such as the breathing, the heart rate, the body motion and the body temperature of the infant Hm, can be also displayed on the portable terminal 2.

Furthermore, an alert for the abnormality in the infant Hm, and a notification such that the body motion sensor 1 is detached from the infant Hm is displayed on a screen region 22 of the portable terminal 2.

By checking the display screen of the portable terminal 2, the childminder can easily check the state of each infant Hm.

Returning to the description with reference to FIG. 1, the portable terminal 2 that operates in accordance with the application program communicates with the cloud server 4, and uploads, to the cloud server 4, the pieces of sensing information on the infant Hm, i.e., a pulse, a body motion, a body temperature, etc., obtained by the body motion sensor 1, and determination information based on those pieces of information, etc.

The portable terminal 3 is an information processing device owned by a parental guardian of the infant Hm, such as a parent. For example, an application program dedicated to the parental guardians is installed in such a terminal.

The parental guardian logs in, from the owing portable terminal 3, a service provided by the application program, enabling them to check the state of their own child (the target infant Hm) through the cloud server 4 on a screen.

The could server 4 analyzes the body situation of the target infant Hm from the sensing information on the infant Hm, generates presentation information to the parental guardian in accordance with such an analysis, and provides such information to the portable terminal 3.

Note that the cloud server 4 may merely relay the sensing information from the body motion sensor 1 and the analysis information from the portable terminal 2, and the application program of the portable terminal 3 may analyze the body situation of the infant Hm from those pieces of information, and may generate and display the presentation information to the parental guardian in accordance with such an analysis.

Figure 4:
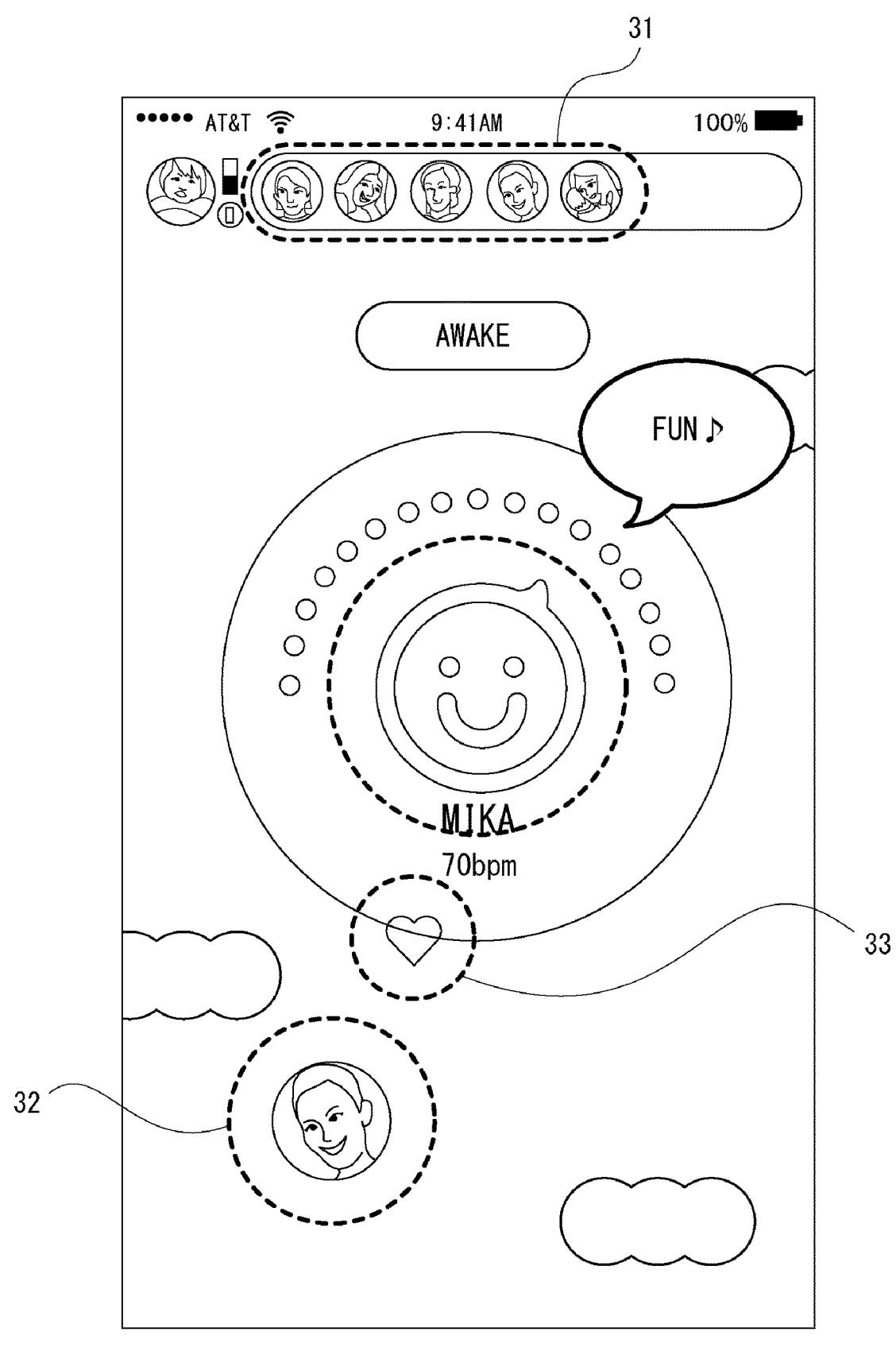
FIG. 4 is a diagram for describing an example screen of the terminal device according to an embodiment.

FIG. 4 illustrates an example display screen on the portable terminal 3 utilized by the parental guardian.

For example, a list of the childminders who take care of the respective infants Hm of the parental guardians is displayed in a screen region 31 of the portable terminal 3, and the childminder who is present near the infant Hm among those childminders is additionally displayed in a region 32. Moreover, various pieces of information, such as the breathing, heart rate, body motion and body temperature, of the infant Hm are also displayed in a region 33. In FIG. 4, as an example, the pulse of the infant Hm is displayed in a real-time manner.

The parental guardian can check the situation of the infant Hm in a real-time manner even apart therefrom by checking the displayed screen on the portable terminal 3.

2. STRUCTURE OF BODY MOTION SENSOR

An example structure of the body motion sensor 1 according to this embodiment will be described with reference to FIG. 5.

Figure 5:
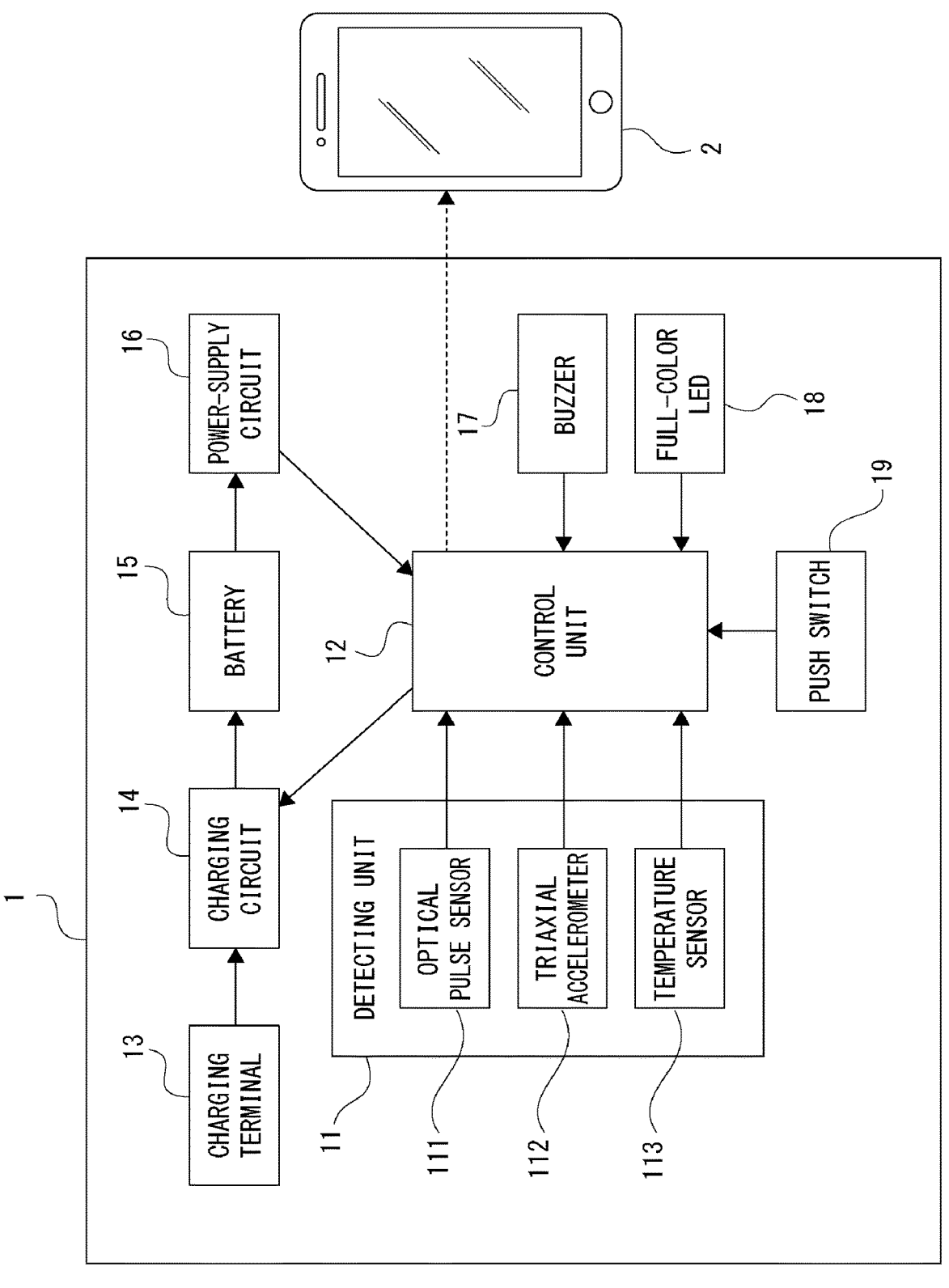
FIG. 5 is a block diagram illustrating the structure of a body motion sensor according to an embodiment.

FIG. 5 is a block diagram illustrating an example structure of the body motion sensor 1. The body motion sensor 1 includes a detecting unit 11, a control unit 12, a charging terminal 13, a charging circuit 14, a battery 15, a power-supply circuit 16, a buzzer 17, a full-color Light Emitting Diode (LED) 18, and a push switch 19.

The detecting unit 11 includes, for example, the optical pulse sensor 111, the triaxial accelerometer 112, and the temperature sensor 113.

The optical pulse sensor 111 is utilized in order to detect the pulse (the heart rate) of the infant Hm, the contact state of the body motion sensor 1 with the infant Hm, etc. The optical pulse sensor 111 includes a light emitting unit like an LED, and a light receiving unit like a photodiode, and detects reflected light, etc., that is light from the light emitting unit and reflected by the infant Hm by the light receiving unit.

Note that the optical pulse sensor 111 includes a measuring device of the oxygen level in the blood like a pulse oxymeter, and an optical sensor as an infrared thermometer (a noncontact thermometer), etc.

The triaxial accelerometer 112 is utilized in order to detect the body motions of the infant Hm, such as breathing and sleeping postures. Moreover, the temperature sensor 113 is utilized in order to detect the body temperature, etc., of the infant Hm.

The control unit 12 is loaded with, for example, a Bluetooth Low Energy (BLE), and includes a microcomputer that includes a Central Processing Unit (CPU), a Read Only Memory (ROM), and a Random Access Memory (RAM), etc. The control unit 12 is accomplished by one or a plurality of microcomputers.

The control unit 12 is operated by power supplied from the battery 15 through the power-supply circuit 16. The charging terminal 13 is connected to the charging circuit 14, and the built-in battery 15 can be charged through the charging circuit 14.

Moreover, the control unit 12 controls the operation of the charging circuit 14, the sound output by the buzzer 17, and the light emission by the full-color LED 18. Furthermore, by detecting the operation given to the push switch 19, the control unit 12 performs power ON and OFF control on the body motion sensor 1.

Furthermore, the control unit 12 constantly monitors the detection signals from the optical pulse sensor 111, the triaxial accelerometer 112 and the temperature sensor 113, and executes a process in accordance with such signals.

For example, the control unit 12 may directly transmit the detection signal of each of these sensors to the portable terminal 2 as it is, or may transmit information obtained by analyzing the detection signal of each sensor to the portable terminal 2.

According to this embodiment, in the body motion sensor 1 that includes each of the above-described structural components, the control unit 12 achieves a process of preventing an alert originating from a false detection.

A conventional afternoon-nap sensor (the body motion sensor) that utilizes the triaxial accelerometer 112 is unable to detect a body motion when released (detached) from the body of a wearing person, and is likely to cause a false operation. Moreover, detection is not enabled only by the triaxial accelerometer 112 when separated from the body of a wearing person.

When a false operation occurs frequently, the childminder who takes care of the infant Hm during a nap (an afternoon-nap) in a nursery school where the afternoon-nap sensor is introduced is not able to take care of such an infant at ease, which disrupts the work of the childminder.

Note that the term false operation means that an alert (sound, light, image display, etc.), which is primarily to be generated when there is no body motion, is generated when the infant Hm is not in an abnormal condition.

Hence, according to the body motion sensor 1 of this embodiment, while the sensing information on the infant Hm is detected using the triaxial accelerometer 112 and also the optical pulse sensor 111 that measures a pulse, etc., a distance from the body of the infant Hm is determined based on the receiving light intensity of the optical pulse sensor 111. When the receiving light intensity is low, a determination is made that it is released (the body motion sensor 1 is detached), and instead of an alert, a "notification of detachment of body motion sensor" is displayed on the screen of the portable terminal 2 as illustrated in FIG. 3.

3. EXAMPLE PROCESS ACCORDING TO THIS EMBODIMENT

Example processes executed by the above-described control unit 12 in this embodiment will be described with reference to FIG. 6 to FIG. 8.

Figure 6:
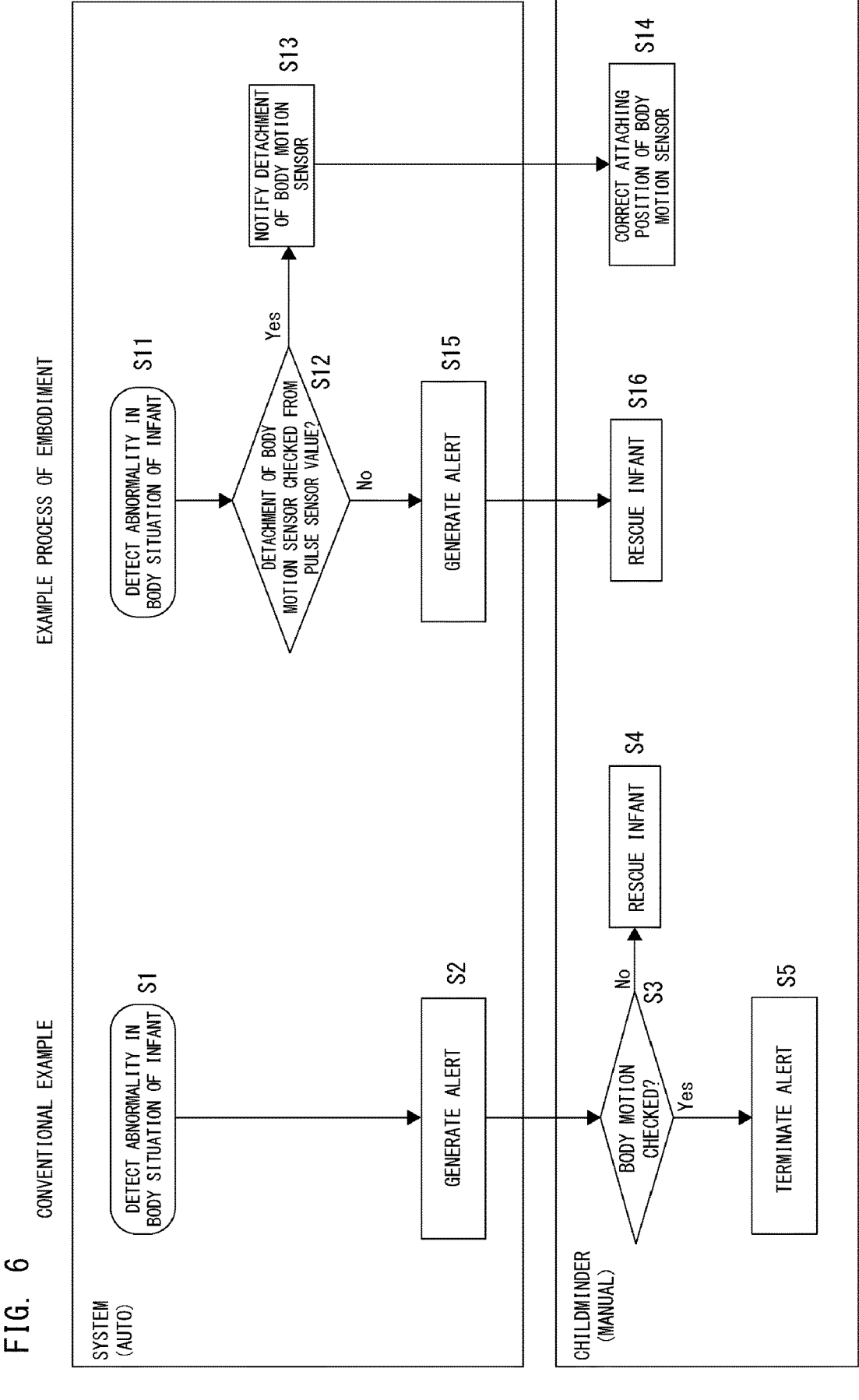
FIG. 6 is a flowchart of a process by the body motion sensor according to an embodiment.

FIG. 6 illustrates example processes by the control unit 12, and actions of the childminder according to this embodiment together with a conventional example.

According to the conventional example, as illustrated in the left side of FIG. 6, when, for example, the detection value of the triaxial accelerometer 112 becomes smaller than a set value, an abnormality in the infant Hm is detected in step S1, and an alert is generated in step S2. The childminder who checked the alert from the portable terminal 2 directly checks the body motion of the infant Hm in step S3, and when the infant Hm is in an abnormal condition, a rescue procedure is taken in step S4, and when there is no abnormality in the infant Hm, the alert is terminated in step S5 since it is a false operation.

Conversely, according to this embodiment, as illustrated in the right side of FIG. 6, when, for example, the detection value of the triaxial accelerometer 112 becomes smaller than the set value in step S11, the control unit 12 determines the receiving light intensity of the optical pulse sensor 111 in step S12, and determines whether or not the device (the body motion sensor 1 itself) is detached from the skin of the infant Hm.

Next, when a determination is made that it is detached, instead of generating an alert, a notification (non-contact information) of the detachment of the body motion sensor 1 is transmitted to the portable terminal 2 in step S13. In this case, on the portable terminal 2, the attachment abnormality in the body motion sensor 1 is notified by screen display, voice output, or vibration, etc. Accordingly, the childminder can check the detachment of the body motion sensor 1 from the infant Hm without any panic in step S14, and can correct the attachment state.

Moreover, when detecting that the detection value of the triaxial accelerometer 112 becomes smaller than the set value and determines as not the detachment of the body motion sensor 1, the control unit 12 transmits, as an alert generation, an alert notification to the portable terminal 2 in step S15. Furthermore, the body motion sensor 1 itself also outputs an alert by the buzzer 17 or the full-color LED 18 illustrated in FIG. 5.

On the portable terminal 2, the childminder is notified of the abnormal condition by the output alert, such as screen display, voice output or vibration, etc. Accordingly, the childminder can immediately check the infant Hm, and can take a rescue procedure as needed in step S16.

Subsequently, the details of the example processes by the control unit 12 according to this embodiment will be described with reference to FIG. 7.

First, the control unit 12 obtains detection signals (pieces of sensing information) from the detecting unit 11 (the optical pulse sensor 111, the triaxial accelerometer 112 and the temperature sensor 113) in step S101.

Next, the control unit 12 determines whether or not there is an abnormality in the infant Hm based on the obtained sensing information in step S102.

For example, as illustrated in FIG. 8, the control unit 12 detects the abnormality in breathing of the infant Hm based on the detection signal (the sensing information) obtained from the triaxial accelerometer 112. More specifically, the control unit 12 detects the presence or absence of the breathing of the infant Hm based on the maximum value of the detection value of acceleration and the minimum value thereof, and the value of a Fast Fourier Transform (FET) of the detection value. The control unit 12 detects that the infant Hm is in an abnormal condition with, for example, the above-described detection value and value of the FFT being respectively equal to or smaller than respective predetermined values.

Although it is not illustrated in the figure, the control unit 12 detects a sleeping posture of the infant Hm, e.g., whether or not it is sleeping on its stomach, based on the detection value of the acceleration. The control unit 12 may detect that the infant Hm is in an abnormal condition with the infant Hm sleeping on its stomach.

Moreover, the control unit 12 detects the abnormality in pulse (heart rate) of the infant Hm based on the detection signal (the sensing information) obtained from the optical pulse sensor 111. More specifically, the control unit 12 detects the presence or absence of the breathing of the infant Hm based on the light intensity and the value of the FFT of such a light intensity. The control unit 12 detects that the infant Hm is in an abnormal condition with, for example, the above-described light intensity and value of the FFT being respectively outside the respective predetermined value ranges.

Although it is not illustrated in the figure, the control unit 12 may obtain the body temperature of the infant Hm from the temperature sensor 113, and may detect that the infant Hm is in an abnormal condition with, for example, the body temperature being outside the predetermined value range.

As described above, the abnormality in the infant Hm is detected based on the sensing information from each sensor.

Moreover, in determining the abnormality in the infant Hm, when the body motion sensor 1 is detached from the clothing of the infant Hm, the detection value of the acceleration, the value of the FFT thereof, the value of the light intensity and the value of the FFT thereof may respectively become values from which the abnormality in the infant Hm is conceivable. In such a case, the control unit 12 may tentatively determine that there is the abnormality in the infant Hm.

Figure 7:
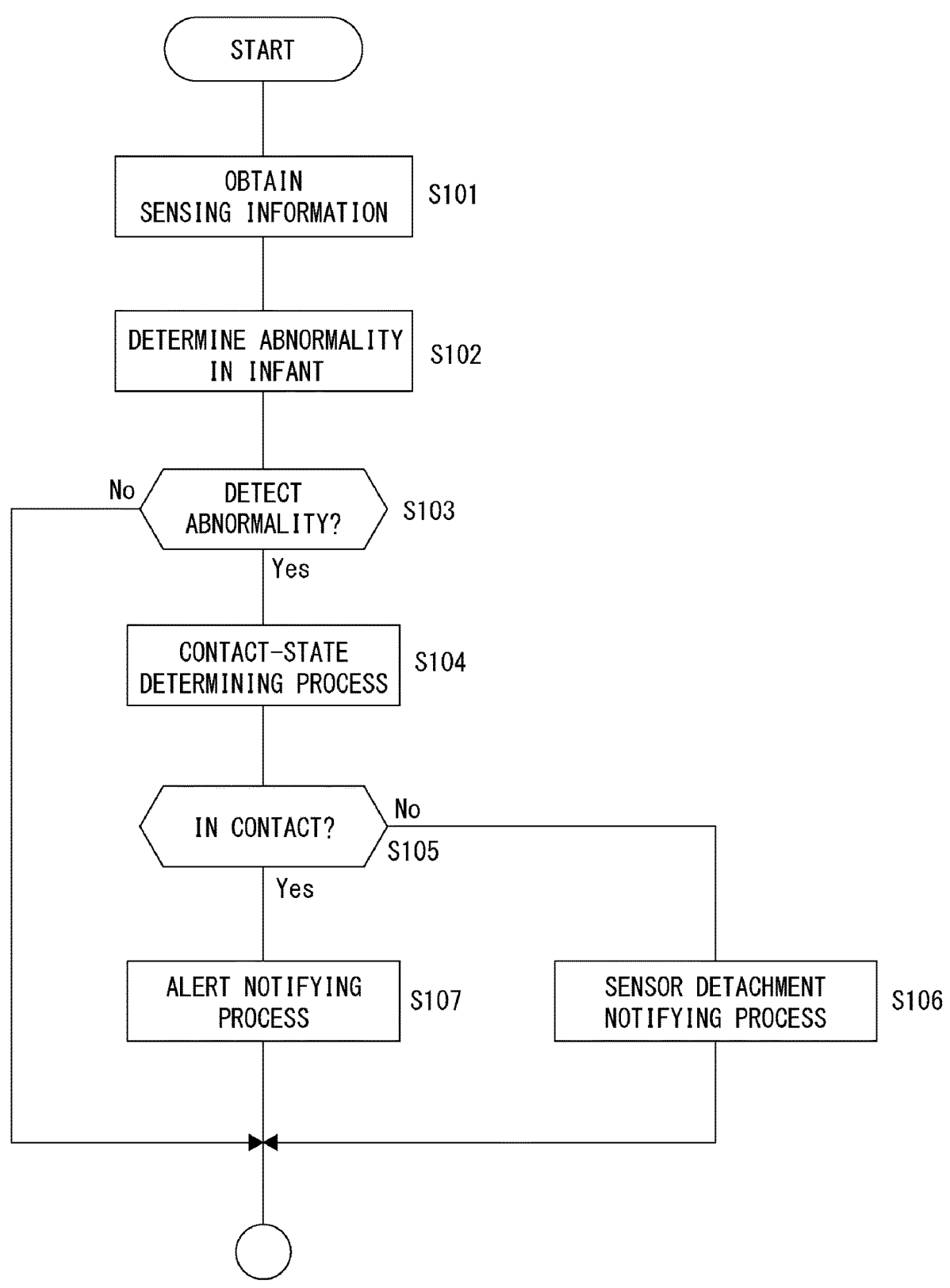
FIG. 7 is a flowchart of the process by the body motion sensor according to an embodiment.

When the abnormality in the infant Hm is not detected through the above-described process in the step S102, the control unit 12 terminates the processes in FIG. 7. That is, since the infant Hm is in a normal condition, an alert or a notification of the detachment of the body motion sensor 1 is not given to the portable terminal 2.

Conversely, when the abnormality in the infant Hm is detected in the step S102, the control unit 12 progresses the process to step S104, and executes a contact-state determining process.

In the contact-state determining process, the control unit 12 determines a contact state of the casing 10 with the skin of the infant Hm based on the detection signal (the light intensity) of the optical pulse sensor 111.

When determining that the casing 10 is not in contact with the body of the infant Hm at this time (i.e., it is in a non-contact state), the control unit 12 progresses the process to steps S105 and S106 in this sequence, and transmits, to the portable terminal 2, the notification (non-contact information) of the detachment of the body motion sensor 1. In this case, on the portable terminal 2, a notification on the abnormality in attachment of the body motion sensor 1 is given by screen display, voice output, or vibration, etc.

After the above-described process in the step S106, the control unit 12 terminates the processes in FIG. 7.

Conversely, when determining that the casing 10 is in contact with the skin of the infant Hm, the control unit 12 progresses the process to steps S105 and S107 in this sequence, and transmits, to the portable terminal 2, the alert information indicating the abnormality in the infant Hm. On the portable terminal 2, the childminder is notified of the abnormal condition by an alert, such as screen display, voice output or vibration, etc.

Moreover, the control unit 12 also executes an operation control so as to cause the buzzer 17 and the full-color LED 18 to respectively output the alert at this time.

After the above-described process in the step S107, the control unit 12 terminates the processes in FIG. 7.

Note that an example case in which the determination on the detachment of the body motion sensor 1 is made upon detection of the abnormality in the infant Hm has been described above, the event to make a determination on the body motion sensor 1 is not limited to this example. For example, whether or not the body motion sensor 1 is detached may be determined at a constant cycle, and when a determination that the body motion sensor 1 is detached is made, the notification of the detachment of the body motion sensor 1 may be given (see an item B in FIG. 8).

Moreover, the contact-state determining process for the body motion sensor 1 and the determining process for the abnormality in the infant may be executed in parallel. In this case, when both the detachment of the body motion sensor 1 and the abnormality in the infant are simultaneously detected, the notifying process of the alert information indicating the abnormality in the infant Hm may be preferentially executed (see items from F to I in FIG. 8).

Furthermore, the processes corresponding to those in FIG. 7 may be executed at the portable terminal 2 or at the portable terminal 3.

For example, the body motion sensor 1 transmits the detection values from the optical pulse sensor 111 and the triaxial accelerometer 112, etc., to the portable terminal 2 at a certain interval (e.g., several second interval). When obtaining the detection values from the body motion sensor 1, the CPU of the portable terminal 2 executes the processes in FIG. 7, decides whether to give an alert or to give the notification of the detachment of the body motion sensor 1, and presents such alert or notification. The same advantageous effects as described above can be also obtained by such operations.

That is, such processes can be accomplished by installing an application program in the portable terminal 2, the application program causing an arithmetic processing device (a CPU, etc.) to execute a process of obtaining the detection signal from one or a plurality of the detecting units 11 which is placed in the casing 10 that can be attached so as to be in contact with a body and which can detect the body situation, and a process of determining the contact state of the casing 10 with the body of the infant Hm based on the detection signal from the optical pulse sensor 111 that is one of the detecting units 11, and of deciding the information content to be output based on the detection signal from the detecting unit 11 in accordance with the determination result. The same is true of the portable terminal 3.

4. MODIFIED EXAMPLE OF SYSTEM CONFIGURATION

Other example configurations of the information presentation system 100 according to the embodiment will be described with reference to FIG. 9 and FIG. 10.

10

Figure 9:
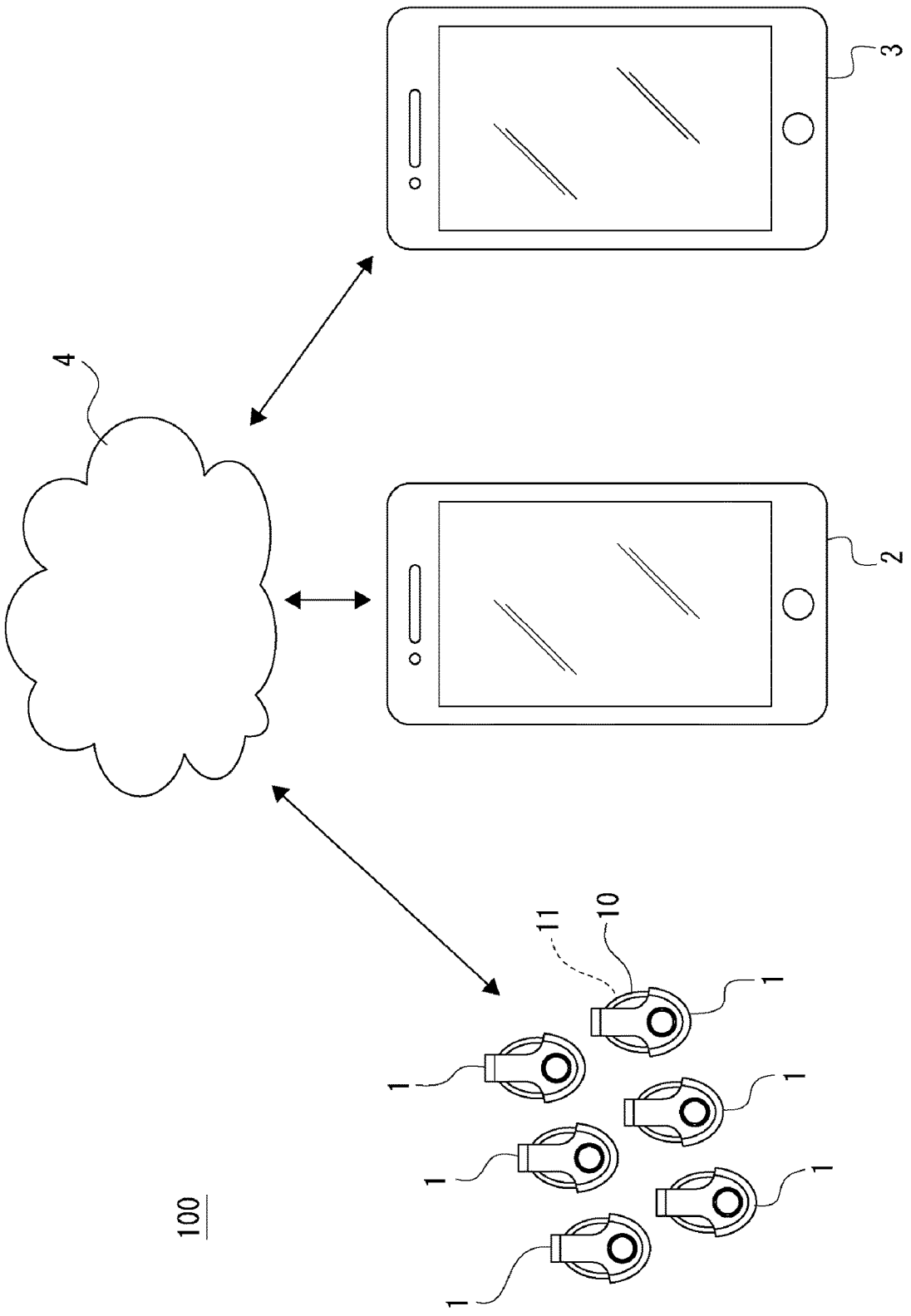
FIG. 9 is a diagram for describing another example system configuration according to an embodiment.
Figure 10:
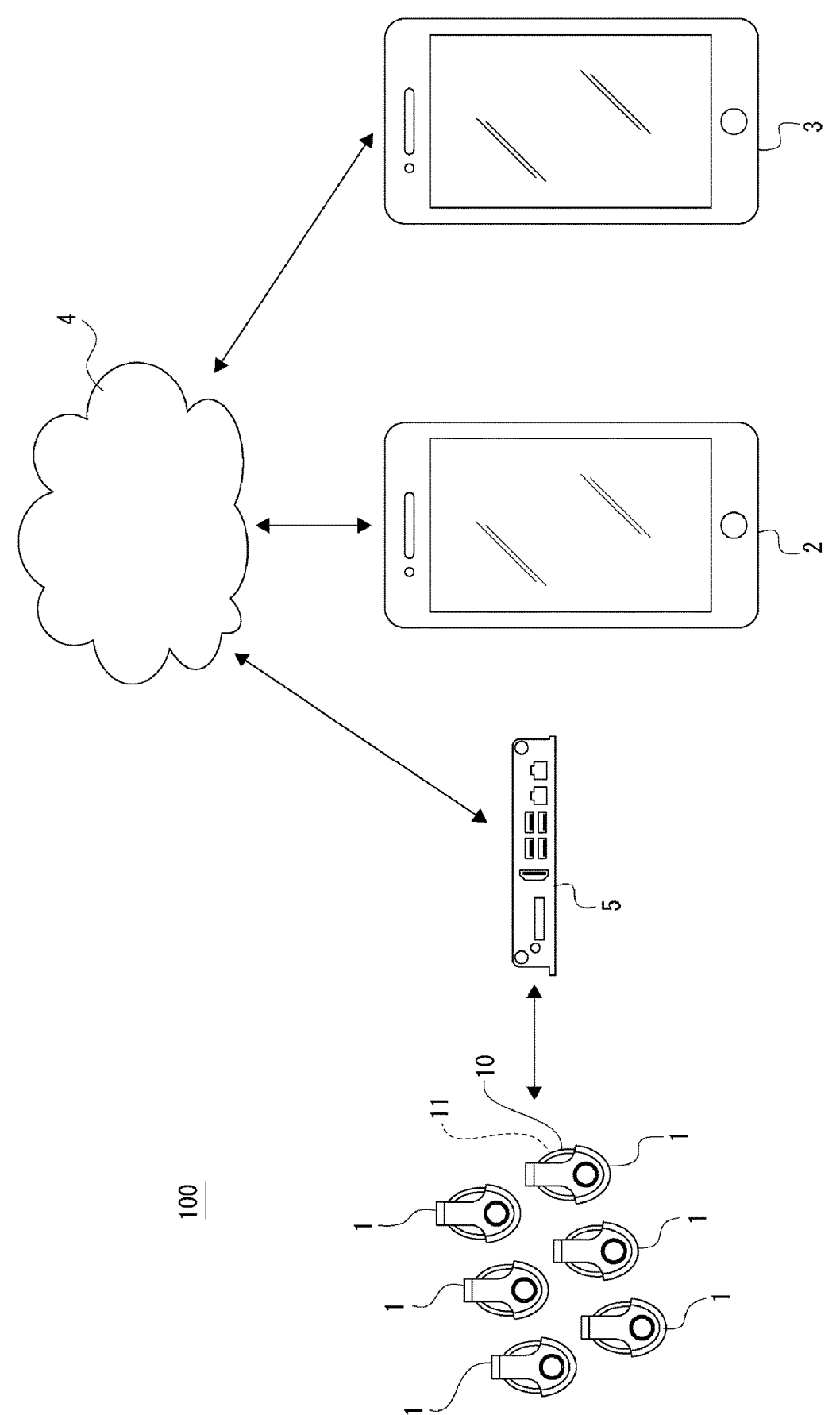
FIG. 10 is a diagram for describing another example system configuration according to an embodiment.

In the information presentation system 100 according to the embodiment, as illustrated in FIG. 9, the body motion sensor 1 may directly communicate with the cloud server 4 by communication, such as Wi-Fi or LTE, etc. Moreover, as illustrated in FIG. 10, the body motion sensor 1 may communicate with the cloud server 4 through a gateway 5.

Furthermore, the pieces of sensing information obtained by the body motion sensor 1 may be gathered and learned at the cloud server 4, so that an individual determination for each infant Hm is enabled. Accordingly, an abnormality determination based on the determination reference set for each infant Hm can be made, and the detection precision of the abnormality in the infant Hm can be improved.

5. SUMMARY

The body motion sensor 1 according to the embodiment as descried above includes one or a plurality of detecting units 11 which is placed in the casing 10 attachable so as to be in contact with the body of a wearing person (infant Hm), and which is capable of detecting the body situation (sensing information) of the infant Hm, and the control unit 12 capable of controlling a transmission of information to an external device (e.g., the portable terminal 2) based on the detection signal from the detecting unit 11 (see FIG. 5).

Moreover, the detecting unit 11 includes at least an optical sensor (the optical pulse sensor 111), and the control unit 12 determines the contact state of the casing 10 with the body of the infant Hm in accordance with the detection signal from the optical pulse sensor 111, and decides the information content to be transmitted to, for example, the portable terminal 2 based on the detection signal from the detecting unit 11 in accordance with the determination result (see from S104 to S107 in FIG. 7).

Hence, the information content to be transmitted to the portable terminal 2 is decided with not only the body situation of the infant Hm but also the contact state of the casing 10 that includes the detecting unit 11 with the body of the infant Hm being taken into consideration.

That is, even if the abnormalities in breathing, pulse, body motion, a sleeping posture, and body temperature, etc., of the infant Hm are detected from the detected pieces of sensing information, a determination on whether such abnormalities are falsely detected due to the detachment of the body motion sensor 1 from the body of the infant Hm or not can be made. Accordingly, when the determination is made that it is a false detection, it becomes possible not to transmit the alert information to the portable terminal 2 utilized by the childminder or the babysitter.

Hence, a false detection can be addressed, and the work burdens for the childminder, etc., and the childcare burdens for the parental guardian can be reduced by appropriate output of alert information.

Moreover, according to the body motion sensor 1 of the embodiment, the control unit 12 determines the contact state of the casing 10 with the body of the infant Hm when detecting the abnormality in the infant Hm based on the body situation of the infant Hm detected by the detecting unit 11 (see S104 in FIG. 7).

When determining that the casing 10 is in contact with the body of the infant Hm, the control unit 12 transmits, to the portable terminal 2, the alert information indicating the abnormality in the infant Hm, and when determining that the casing 10 is not in contact with the body of the infant Hm, transmits, to the portable terminal 2, the notification signal indicating the non-contact state (see from S105 to S107 in FIG. 7).

Accordingly, even if the abnormality in the infant Hm is detected, if it is in a non-contact state, the alert information is not to be transmitted to the portable terminal 2.

Hence, occasions in which the childminder, etc., comes on the run to the infant to check the situation although the infant Hm is in a normal condition are reduced, and thus the work burdens and the psychological burdens for the childminder, etc., can be reduced.

Note that according to the embodiment, although the object to which the body motion sensor 1 is attached is the clothing of the infant Hm, the body motion sensor 1 can be attached to various objects as far as it has a thickness like fabric, such as the clothing of an adult and that of an aged person in addition to the infant Hm, the clothing of an animal and the curtain of a room.

Eventually, the advantageous effects described in the present disclosure are merely examples and are not limited to any particular one. The other advantageous effect may be accomplished or only some of the advantageous effects described in the present disclosure may be accomplished. Moreover, the embodiment disclosed in the present disclosure is merely an example, and the present invention is not limited to such embodiment. Hence, various changes can be made in accordance with a design, etc., as the embodiment other than the above-described embodiment without departing from the scope and spirit of the present invention. Note that the combination of all structures described in the embodiment are not always requisite to address the technical problem.

REFERENCE SIGNS LIST

1 Body motion sensor
2 Portable terminal
3 Portable terminal
4 Cloud server
10 Casing
11 Detecting unit
12 Control unit
100 Information presentation system
111 Optical pulse sensor
112 Triaxial accelerometer
Hm Infant

The invention claimed is:

1. A body motion sensor, comprising:
at least one sensor which is placed in a casing, the casing being attachable and configured to be in contact with a body of a wearing person, the at least one sensor being capable of detecting a body situation of the wearing person; and
a processor capable of controlling a transmission of information to an external device based on at least one detection signal from the at least one sensor,
wherein the at least one sensor comprises at least an optical sensor,
wherein the processor detects an abnormality in the wearing person in accordance with a first detection signal from the at least one sensor,
wherein the processor determines a contact state of the casing with the body of the wearing person in accordance with a second detection signal from the optical sensor, and decides an information content to be transmitted to the external device based on the at least one detection signal from the at least one sensor in accordance with a determination result of the contact state,
wherein the processor transmits an alert indicating the abnormality, as the information content to be transmitted to the external device, in response to the abnormality being detected in accordance with the first detection signal and the determination result indicating that the contact state is in contact with the body of the wearing person, and
wherein the processor only determines the contact state of the casing with the body of the wearing person in accordance with the second detection signal after the abnormality in the wearing person is detected in accordance with the first detection signal.

2. The body motion sensor according to claim 1, wherein the processor:
determines the contact state of the casing with the body of the wearing person when detecting the abnormality in the wearing person based on the body situation of the wearing person detected by the at least one sensor;
when determining that the casing is in contact with the body of the wearing person, transmits, to the external device, the alert information indicating the abnormality in the wearing person; and
when determining that the casing is not in contact with the body of the wearing person, transmits, to the external device, non-contact information.

3. A non-transitory computer-readable storage medium storing a program that causes an arithmetic processing device to execute:
obtaining at least one detection signal from at least one sensor which is placed in a casing, the casing being attachable and configured to be in contact with a body of a wearing person, the at least one sensor being capable of detecting a body situation of the wearing person;
detecting an abnormality in the wearing person in accordance with a first detection signal from the at least one sensor;
determining a contact state of the casing with the body of the wearing person in accordance with a second detection signal from an optical sensor that is one of the at least one sensor; and
deciding an information content to be output based on the at least one detection signal from the at least one sensor in accordance with a determination result of the contact state,
wherein the arithmetic processing device transmits an alert indicating the abnormality, as the information content to be output, in response to the abnormality being detected in accordance with the first detection signal and the determination result indicating that the contact state is in contact with the body of the wearing person, and
wherein the arithmetic processing device only determines the contact state of the casing with the body of the wearing person in accordance with the second detection signal after the abnormality in the wearing person is detected in accordance with the first detection signal.

4. An information presentation system, comprising:
a body motion sensor comprising:
at least one sensor which is placed in a casing, the casing being attachable and configured to be in contact with a body of a wearing person, the at least one sensor being capable of detecting a body situation of the wearing person;
a processor capable of controlling a transmission of information to an external device based on at least one detection signal from the at least one sensor; and
an optical sensor as at least one of the at least one sensor; and a terminal device presenting information based on the information transmitted from the body motion sensor, wherein the processor detects an abnormality in the wearing person in accordance with a first detection signal from the at least one sensor, wherein a contact state of the casing with the body of the wearing person is determined in accordance with a second detection signal from the optical sensor, wherein a presentation content by the terminal device is decided in accordance with a determination result of the contact state, wherein the processor transmits an alert indicating the abnormality, as the presentation content to be presented by the terminal device, in response to the abnormality being detected in accordance with the first detection signal and the determination result indicating that the contact state is in contact with the body of the wearing person, and wherein the processor only determines the contact state of the casing with the body of the wearing person in accordance with the second detection signal after the abnormality in the wearing person is detected in accordance with the first detection signal.

* * * * *